(12) United States Patent
Wright et al.

(10) Patent No.: US 11,559,213 B2
(45) Date of Patent: Jan. 24, 2023

(54) MEDICAL DEVICE WITH PRESSURE SENSOR

(71) Applicant: BOSTON SCIENTIFIC SCIMED, INC., Maple Grove, MN (US)

(72) Inventors: Cory P. Wright, Woodbury, MN (US); Nathaniel Stark, Plymouth, MN (US); Wenguang Li, Los Gatos, CA (US); Gaylin Mildred Yee, Newark, CA (US); Neil Pollock, Hertfordshire (GB); Mikhail E. Bashtanov, Cambridge (GB); Fahad Hussain, Hertfordshire (GB); Mette Funding La Cour, Cambridge (GB)

(73) Assignee: Boston Scientific Scimed, Inc., Maple Grove, MN (US)

( * ) Notice: Subject to any disclaimer, the term of this patent is extended or adjusted under 35 U.S.C. 154(b) by 964 days.

(21) Appl. No.: 16/376,698

(22) Filed: Apr. 5, 2019

(65) Prior Publication Data
US 2019/0307338 A1    Oct. 10, 2019

Related U.S. Application Data

(60) Provisional application No. 62/653,921, filed on Apr. 6, 2018.

(51) Int. Cl.
*A61B 8/00*       (2006.01)
*A61B 5/0215*     (2006.01)
(Continued)

(52) U.S. Cl.
CPC ........ *A61B 5/02154* (2013.01); *A61B 5/0084* (2013.01); *A61B 5/6851* (2013.01);
(Continued)

(58) Field of Classification Search
CPC combination set(s) only.
See application file for complete search history.

(56) References Cited

U.S. PATENT DOCUMENTS 3,273,447 A    9/1966 Wallace
3,963,323 A    6/1976 Arnold
(Continued)

FOREIGN PATENT DOCUMENTS

CN    102469943 A    5/2012
CN    102519663 A    6/2012
(Continued)

OTHER PUBLICATIONS

International Search report and Written Opinion dated May 29, 2017 for International Application No. PCT/US2017/018905.
International Search Report and Written Opinion dated Oct. 22, 2018 for International Application No. PCT/US2018/044153.
(Continued)

*Primary Examiner* — Joel F Brutus
(74) *Attorney, Agent, or Firm* — Seager, Tufte & Wickhem LLP (57) ABSTRACT

Pressure sensing guidewires and methods for making and using pressure sensing guidewires are disclosed. An example pressure sensing guidewire may include a tubular member having a proximal region and a housing region. An optical fiber may be disposed within the tubular member and extend to the housing region. The optical fiber may have a distal end region with a cavity formed therein. A polymeric member disposed within the cavity. A reflective surface disposed along the polymeric member.

19 Claims, 5 Drawing Sheets

(51) Int. Cl.
*A61B 5/00* (2006.01)
*A61M 25/09* (2006.01)
*G02B 6/36* (2006.01)
*A61M 25/00* (2006.01)

(52) U.S. Cl.
CPC ..... *A61M 25/09* (2013.01); *A61B 2562/0247* (2013.01); *A61B 2562/12* (2013.01); *A61M 2025/0002* (2013.01); *A61M 2025/09133* (2013.01); *G02B 6/3624* (2013.01)

(56) References Cited

U.S. PATENT DOCUMENTS

| | | |
|---|---|---|
| 4,112,941 A | 9/1978 | Larimore |
| 4,487,206 A | 12/1984 | Aagard |
| 4,711,246 A | 12/1987 | Alderson |
| 4,771,782 A | 9/1988 | Millar |
| 4,893,630 A | 1/1990 | Roberts, Jr. |
| 4,953,553 A | 9/1990 | Tremulis |
| 5,005,584 A | 4/1991 | Little |
| 5,106,455 A | 4/1992 | Jacobsen et al. |
| 5,135,503 A | 8/1992 | Abrams |
| 5,178,159 A | 1/1993 | Christian |
| 5,238,004 A | 8/1993 | Sahatjian et al. |
| 5,280,786 A | 1/1994 | Wlodarczyk |
| 5,313,957 A | 5/1994 | Little |
| 5,322,064 A | 6/1994 | Lundquist |
| 5,414,507 A | 5/1995 | Herman |
| 5,421,195 A | 6/1995 | Wlodarczyk |
| 5,422,969 A | 6/1995 | Eno |
| 5,425,371 A | 6/1995 | Mischenko |
| 5,427,114 A | 6/1995 | Colliver et al. |
| 5,437,288 A | 8/1995 | Schwartz |
| 5,438,873 A | 8/1995 | Wlodarczyk et al. |
| 5,450,853 A | 9/1995 | Hastings |
| 5,573,520 A | 11/1996 | Schwartz et al. |
| 5,633,963 A | 5/1997 | Rickenbach et al. |
| 5,748,819 A | 5/1998 | Szentesi et al. |
| 5,755,668 A | 5/1998 | Itoigawa et al. |
| 5,772,609 A | 6/1998 | Nguyen et al. |
| 5,779,698 A | 7/1998 | Clayman |
| 5,797,856 A | 8/1998 | Frisbie et al. |
| 5,836,885 A | 11/1998 | Schwager |
| 5,865,801 A | 2/1999 | Houser |
| 5,872,879 A | 2/1999 | Hamm |
| 5,873,835 A | 2/1999 | Hastings et al. |
| 5,902,248 A | 5/1999 | Millar et al. |
| 5,916,177 A | 6/1999 | Schwager |
| 5,938,624 A | 8/1999 | Akerfeldt et al. |
| 5,949,929 A | 9/1999 | Hamm |
| 5,964,714 A | 10/1999 | Lafontaine |
| 6,112,598 A | 9/2000 | Tenerz et al. |
| 6,120,457 A | 9/2000 | Coombes et al. |
| 6,139,510 A | 10/2000 | Palermo |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,312,380 B1 | 11/2001 | Hoek et al. |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,461,301 B2 | 10/2002 | Smith |
| 6,506,313 B1 | 1/2003 | Fetterman et al. |
| 6,508,803 B1 | 1/2003 | Horikawa et al. |
| 6,565,514 B2 | 5/2003 | Svanerudh et al. |
| 6,575,911 B1 | 6/2003 | Schwager |
| 6,579,246 B2 | 6/2003 | Jacobsen et al. |
| 6,579,484 B1 | 6/2003 | Tiernan et al. |
| 6,585,660 B2 | 7/2003 | Dorando et al. |
| 6,589,164 B1 | 7/2003 | Flaherty |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B2 | 8/2004 | Bartlett |
| 6,908,442 B2 | 6/2005 | von Malmborg et al. |
| 6,918,873 B1 | 7/2005 | Millar et al. |
| 6,918,882 B2 | 7/2005 | Skujins et al. |
| 6,925,213 B2 * | 8/2005 | Boyd .................. G01L 9/0079 385/12 |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,244,244 B2 | 7/2007 | Racenet et al. |
| 7,259,862 B2 | 8/2007 | Duplain |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth et al. |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 | 8/2010 | Ainsworth et al. |
| 7,878,984 B2 | 2/2011 | Jacobsen et al. |
| 7,930,014 B2 | 4/2011 | Huenneckens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 | 1/2013 | Sela et al. |
| 8,393,802 B2 | 3/2013 | Stanley et al. |
| 8,410,940 B2 | 4/2013 | Samuelsson et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,491,484 B2 | 7/2013 | Lewis |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,585,613 B2 | 11/2013 | Nagano |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,757,893 B1 | 6/2014 | Isenhour et al. |
| 8,764,683 B2 | 7/2014 | Meller et al. |
| 8,781,193 B2 | 7/2014 | Steinberg et al. |
| 8,855,744 B2 | 10/2014 | Tolkowsky et al. |
| 8,920,870 B2 | 12/2014 | Weber |
| 8,936,401 B2 | 1/2015 | Belleville et al. |
| 8,998,823 B2 | 4/2015 | Manstrom et al. |
| 9,010,286 B2 | 4/2015 | Novak |
| RE45,534 E | 6/2015 | Huennekens et al. |
| 9,052,466 B2 | 6/2015 | Belleville et al. |
| 9,095,313 B2 | 8/2015 | Tolkowsky et al. |
| 9,110,255 B2 | 8/2015 | Lin et al. |
| 9,149,230 B2 | 10/2015 | Caron |
| 9,289,137 B2 | 3/2016 | Corl |
| 9,339,348 B2 | 5/2016 | Davies et al. |
| 9,364,153 B2 | 6/2016 | Merritt et al. |
| 9,375,164 B2 | 6/2016 | Tolkowsky et al. |
| 9,629,571 B2 | 4/2017 | Tolkowsky et al. |
| RE46,562 E | 10/2017 | Huennekens et al. |
| 9,855,384 B2 | 1/2018 | Cohen et al. |
| 9,907,527 B2 | 3/2018 | Dascal et al. |
| 9,974,443 B2 | 5/2018 | Merritt et al. |

(56) References Cited

U.S. PATENT DOCUMENTS

| | | |
|---|---|---|
| 10,076,301 B2 | 9/2018 | Millett et al. |
| 10,098,702 B2 | 10/2018 | Merritt et al. |
| 10,130,310 B2 | 11/2018 | Alpert et al. |
| 2002/0013527 A1 | 1/2002 | Hoek |
| 2003/0031422 A1 | 2/2003 | Inagaki et al. |
| 2003/0069522 A1 | 4/2003 | Jacobsen et al. |
| 2003/0120175 A1 | 6/2003 | Ehr |
| 2003/0159518 A1 | 8/2003 | Sawatari |
| 2004/0006277 A1 | 1/2004 | Langenhove et al. |
| 2004/0073141 A1 | 4/2004 | Hartley et al. |
| 2004/0181174 A2 | 9/2004 | Davis et al. |
| 2004/0258370 A1 | 12/2004 | Bush |
| 2005/0000294 A1 | 1/2005 | Tenerz et al. |
| 2005/0141817 A1 | 6/2005 | Yazaki et al. |
| 2006/0052700 A1 | 3/2006 | Svanerudh |
| 2006/0074318 A1 | 4/2006 | Ahmed et al. |
| 2006/0122537 A1 | 6/2006 | Reynolds et al. |
| 2007/0010726 A1 | 1/2007 | Loeb |
| 2007/0055162 A1 | 3/2007 | Vlahos |
| 2008/0119758 A1 | 5/2008 | Samuelsson et al. |
| 2008/0285909 A1 | 11/2008 | Younge et al. |
| 2009/0082678 A1 | 3/2009 | Smith |
| 2009/0088650 A1 | 4/2009 | Corl |
| 2009/0116020 A1 | 5/2009 | Wu et al. |
| 2009/0192412 A1 | 7/2009 | Sela et al. |
| 2009/0226128 A1 | 9/2009 | Donlagic et al. |
| 2010/0022950 A1 | 1/2010 | Anderson et al. |
| 2010/0087605 A1 | 4/2010 | Yamamoto et al. |
| 2010/0145308 A1 | 6/2010 | Layman et al. |
| 2010/0234698 A1 | 9/2010 | Manstrom et al. |
| 2010/0241008 A1 | 9/2010 | Belleville et al. |
| 2011/0046477 A1 | 2/2011 | Hulvershorn et al. |
| 2011/0071407 A1 | 3/2011 | Hübinette et al. |
| 2011/0098572 A1 | 4/2011 | Chen et al. |
| 2011/0152721 A1 | 6/2011 | Sela |
| 2011/0178413 A1 | 7/2011 | Schmitt et al. |
| 2011/0186294 A1 | 8/2011 | Narvaez et al. |
| 2011/0229094 A1 | 9/2011 | Isenhour et al. |
| 2011/0245808 A1 | 10/2011 | Voeller et al. |
| 2011/0319773 A1 | 12/2011 | Kanz et al. |
| 2012/0083794 A1 | 4/2012 | Martin et al. |
| 2012/0122051 A1 | 5/2012 | Hackel et al. |
| 2012/0210797 A1* | 8/2012 | Yu .................... G02B 6/4214 264/1.27 |
| 2012/0227505 A1 | 9/2012 | Belleville et al. |
| 2012/0238869 A1 | 9/2012 | Schmitt et al. |
| 2012/0245457 A1 | 9/2012 | Crowley |
| 2012/0259273 A1 | 10/2012 | Moshinsky et al. |
| 2012/0265102 A1 | 10/2012 | Leo et al. |
| 2013/0046190 A1 | 2/2013 | Davies |
| 2013/0051731 A1 | 2/2013 | Belleville et al. |
| 2013/0190633 A1 | 7/2013 | Dorando |
| 2013/0218032 A1 | 8/2013 | Belleville |
| 2013/0296718 A1 | 11/2013 | Ranganathan et al. |
| 2013/0296722 A1 | 11/2013 | Warnking et al. |
| 2013/0317372 A1* | 11/2013 | Eberle ................ A61B 5/0084 600/478 |
| 2013/0345574 A1 | 12/2013 | Davies et al. |
| 2014/0005558 A1 | 1/2014 | Gregorich |
| 2014/0058275 A1 | 2/2014 | Gregorich et al. |
| 2014/0066789 A1 | 3/2014 | Nishigishi et al. |
| 2014/0081244 A1 | 3/2014 | Voeller et al. |
| 2014/0094691 A1 | 4/2014 | Steinberg et al. |
| 2014/0094693 A1 | 4/2014 | Cohen et al. |
| 2014/0103273 A1 | 4/2014 | Nakajima |
| 2014/0107624 A1 | 4/2014 | Belleville |
| 2014/0121475 A1 | 5/2014 | Alpert et al. |
| 2014/0135633 A1 | 5/2014 | Anderson et al. |
| 2014/0180028 A1 | 6/2014 | Burkett |
| 2014/0205235 A1 | 7/2014 | Benjamin et al. |
| 2014/0207008 A1 | 7/2014 | Davies |
| 2014/0241669 A1 | 8/2014 | Belleville et al. |
| 2014/0248021 A1 | 9/2014 | Belleville et al. |
| 2014/0276109 A1 | 9/2014 | Gregorich |
| 2014/0276142 A1 | 9/2014 | Dorando |
| 2014/0309533 A1 | 10/2014 | Yamashika |
| 2014/0350414 A1* | 11/2014 | Mcgowan ............ G02B 6/3604 600/480 |
| 2015/0003783 A1 | 1/2015 | Benjamin et al. |
| 2015/0003789 A1 | 1/2015 | Webler |
| 2015/0025330 A1 | 1/2015 | Davies et al. |
| 2015/0025398 A1 | 1/2015 | Davies et al. |
| 2015/0032011 A1 | 1/2015 | McGowan et al. |
| 2015/0051499 A1 | 2/2015 | McGowan |
| 2015/0078714 A1 | 3/2015 | Isenhour |
| 2015/0080749 A1 | 3/2015 | Anderson et al. |
| 2015/0112210 A1 | 4/2015 | Webler |
| 2015/0119705 A1 | 4/2015 | Tochterman et al. |
| 2015/0133800 A1 | 5/2015 | McCaffrey |
| 2015/0141842 A1 | 5/2015 | Spanier |
| 2015/0161790 A1 | 6/2015 | Takahashi et al. |
| 2015/0164467 A1 | 6/2015 | Suetoshi et al. |
| 2015/0198774 A1 | 7/2015 | Lin et al. |
| 2015/0230713 A1 | 8/2015 | Merritt et al. |
| 2015/0230714 A1 | 8/2015 | Davies et al. |
| 2015/0301288 A1 | 10/2015 | Thornton, Jr. |
| 2015/0305633 A1 | 10/2015 | McCaffrey |
| 2015/0323747 A1 | 11/2015 | Leigh et al. |
| 2016/0008084 A1 | 1/2016 | Merritt et al. |
| 2016/0135757 A1 | 5/2016 | Anderson et al. |
| 2016/0135787 A1 | 5/2016 | Anderson et al. |
| 2016/0136392 A1 | 5/2016 | Wenderow et al. |
| 2016/0157802 A1 | 6/2016 | Anderson |
| 2016/0157803 A1 | 6/2016 | Keller |
| 2016/0157807 A1 | 6/2016 | Anderson et al. |
| 2016/0166327 A1 | 6/2016 | Keller |
| 2016/0206214 A1 | 7/2016 | Davies et al. |
| 2017/0065225 A1 | 3/2017 | Hanson |
| 2018/0192983 A1 | 7/2018 | Dascal et al. |
| 2018/0263507 A1 | 9/2018 | Merritt et al. |
| 2019/0083046 A1 | 3/2019 | Alpert et al. |

FOREIGN PATENT DOCUMENTS

| | | |
|---|---|---|
| CN | 106052913 | 10/2016 |
| DE | 202014100938 U1 | 3/2014 |
| EP | 0235992 A1 | 9/1987 |
| EP | 0738495 A1 | 10/1996 |
| EP | 0879615 A1 | 11/1998 |
| EP | 0879617 A1 | 11/1998 |
| EP | 1039321 A2 | 9/2000 |
| EP | 0750879 B1 | 11/2000 |
| EP | 1136032 A1 | 9/2001 |
| EP | 1136036 A1 | 9/2001 |
| EP | 1136036 B1 | 2/2003 |
| EP | 1136032 B1 | 9/2003 |
| EP | 1479407 A1 | 11/2004 |
| EP | 1925958 A1 | 5/2008 |
| EP | 1927316 A1 | 6/2008 |
| GB | 1440761 A | 6/1976 |
| GB | 2300978 A | 11/1996 |
| JP | 53-141644 A | 12/1978 |
| JP | 08-257128 A | 10/1996 |
| JP | 08-280634 A | 10/1996 |
| JP | 10-501339 A | 2/1998 |
| JP | 10-337280 A | 12/1998 |
| JP | H1172399 A | 3/1999 |
| JP | 11-258476 A | 9/1999 |
| JP | 2005-291945 A | 10/2005 |
| JP | 2007532871 | 11/2007 |
| JP | 2008-304731 A | 12/2008 |
| JP | 2009-10182 A | 1/2009 |
| JP | 2010-233883 A | 10/2010 |
| JP | 2010230669 A | 10/2010 |
| JP | 2013-132886 A | 7/2013 |
| JP | 2014-42645 A | 3/2014 |
| JP | 2015517678 A | 6/2015 |
| WO | 9313707 A1 | 7/1993 |
| WO | 9533983 A1 | 12/1995 |
| WO | 9626671 A1 | 9/1996 |
| WO | 9945352 A1 | 9/1999 |
| WO | 2007/058616 A1 | 5/2007 |
| WO | 2007/130163 A1 | 11/2007 |
| WO | 2008/034010 A2 | 3/2008 |

(56) References Cited

FOREIGN PATENT DOCUMENTS

| WO | 2008/076931 A2 | 6/2008 |
| WO | 2009/042865 A1 | 4/2009 |
| WO | 2011/027282 A1 | 3/2011 |
| WO | 2011/090744 A2 | 7/2011 |
| WO | 2011/123689 A1 | 10/2011 |
| WO | 2012/000798 A1 | 1/2012 |
| WO | 2012/090210 A1 | 7/2012 |
| WO | 2012/091783 A1 | 7/2012 |
| WO | 2013/033489 A1 | 3/2013 |
| WO | 2014/025255 A1 | 2/2014 |
| WO | 2015/059311 A1 | 4/2015 |
| WO | 2016005944 A1 | 1/2016 |
| WO | 2017013020 A1 | 1/2017 |

OTHER PUBLICATIONS

International Search Report and Written Opinion dated May 7, 2019 for International Application No. PCT/US2019/019247.
Van'T Veer et al., "Comparison of Different Diastolic Resting Indexes to iFR. Are They Equal?", Journal of American College of Cardiology, 70(25): 3088-3096, Dec. 18, 2017.
Jaroslaw et al., "Two Stage EMG Onset Detection Method", Archives of Control Sciences, 22(4): 427-440, Dec. 1, 2012.
International Search Report and Written Opinion dated Jun. 19, 2019 for International Application No. PCT/US2019/027512.
International Search Report and Written Opinion dated Jul. 3, 2019 for International Application No. PCT/US2019/023488.
International Search Report and Written Opinion dated Jul. 8, 2019 for International Application No. PCT/US2019/026055.

\* cited by examiner

MEDICAL DEVICE WITH PRESSURE SENSOR

CROSS-REFERENCE TO RELATED APPLICATIONS

This application claims the benefit of priority under 35 U.S.C. § 119 of U.S. Provisional Application No. 62/653,921, filed Apr. 6, 2018, the entire disclosure of which is hereby incorporated by reference.

TECHNICAL FIELD

The present disclosure pertains to medical devices, and methods for manufacturing medical devices. More particularly, the present disclosure pertains to blood pressure sensing guidewires and methods for using pressure sensing guidewires.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A pressure sensing medical device is disclosed. The pressure sensing medical device comprises: a tubular member having a proximal region and a housing region; an optical fiber disposed within the tubular member and extending to the housing region, the optical fiber having a distal end region with a cavity formed therein; a polymeric member disposed within the cavity; and a reflective surface disposed along the polymeric member.

Alternatively or additionally to any of the embodiments above, the proximal region of the tubular member has a first inner diameter, wherein the housing region of the tubular member has a second inner diameter, and wherein the first inner diameter is different from the second inner diameter.

Alternatively or additionally to any of the embodiments above, the first inner diameter is smaller than the second inner diameter.

Alternatively or additionally to any of the embodiments above, the tubular member has a substantially constant outer diameter.

Alternatively or additionally to any of the embodiments above, the optical fiber has a substantially constant outer diameter.

Alternatively or additionally to any of the embodiments above, one or more fiber Bragg gratings are disposed along the optical fiber.

Alternatively or additionally to any of the embodiments above, the polymeric member substantially fills the cavity.

Alternatively or additionally to any of the embodiments above, the reflective surface includes a coating disposed along the polymeric member.

Alternatively or additionally to any of the embodiments above, the coating includes a metal.

Alternatively or additionally to any of the embodiments above, the coating is disposed at a distal end of the polymeric member.

A pressure sensing guidewire is disclosed. The pressure sensing guidewire comprises: a tubular member having a proximal region and a pressure sensor housing region; an optical fiber disposed within the tubular member and extending to the pressure sensor housing region; wherein a pressure sensor is defined by a polymer-filled cavity at a distal end region of the optical fiber; and a reflective coating disposed along at least a portion of the pressure sensor.

Alternatively or additionally to any of the embodiments above, the proximal region of the tubular member has a first inner diameter, wherein the pressure sensor housing region of the tubular member has a second inner diameter, and wherein the first inner diameter is different from the second inner diameter.

Alternatively or additionally to any of the embodiments above, the first inner diameter is smaller than the second inner diameter.

Alternatively or additionally to any of the embodiments above, the tubular member has a substantially constant outer diameter.

Alternatively or additionally to any of the embodiments above, the optical fiber has a substantially constant outer diameter.

Alternatively or additionally to any of the embodiments above, one or more fiber Bragg gratings are disposed along the optical fiber.

Alternatively or additionally to any of the embodiments above, the reflective coating includes a metal.

Alternatively or additionally to any of the embodiments above, the reflective coating is disposed at a distal end of the pressure sensor.

Alternatively or additionally to any of the embodiments above, the proximal region of the tubular member has a first inner diameter, the pressure sensor housing region of the tubular member has a second inner diameter, the first inner diameter is smaller than the second inner diameter, and the tubular member has a substantially constant outer diameter.

A method for manufacturing a pressure sensing guidewire is disclosed. The method comprises: forming a cavity along a distal end region of an optical fiber; disposing a polymeric member within the cavity; coupling a reflective member to the polymeric member to form a pressure sensor; and disposing the pressure sensor within a housing region of a tubular member.

Alternatively or additionally to any of the embodiments above, further comprising disposing one or more fiber Bragg gratings along the optical fiber.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis (and/or the aortic pressure).

Figure 1:
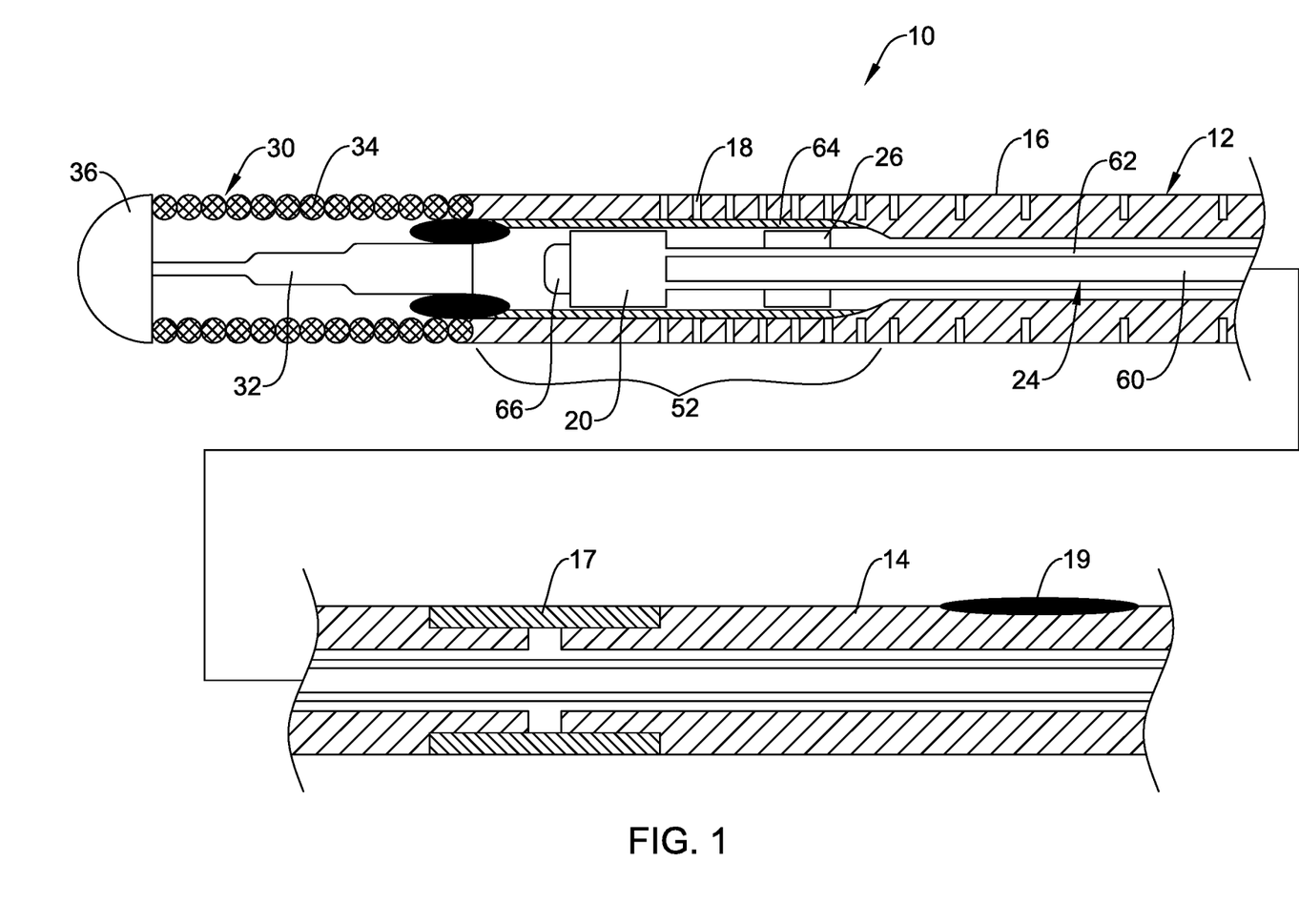
FIG. 1 is a partial cross-sectional side view of a portion of an example medical device.

FIG. 1 illustrates a portion of an example medical device 10. In this example, the medical device 10 is a blood pressure sensing guidewire 10. However, this is not intended to be limiting as other medical devices are contemplated. For example, the medical device 10 may include a variety of devices including catheters, shafts, leads, wires/guidewires, or the like and/or a device designed to be used in a vascular region, body lumen, or the like. As discussed herein, the medical device may include a sensor (e.g., the sensor 20) that may be utilized to measure pressure and/or temperature. In some of these and in other instances, the sensor (e.g., the sensor 20) may be used in conjunction with ultrasound, optical coherence tomography, photoacoustic imaging, or the like.

The guidewire 10 may include a shaft or tubular member 12. The tubular member 12 may include a proximal region 14 and a distal region 16. The materials for the proximal region 14 and the distal region 16 may vary and may include those materials disclosed herein. For example, the distal region 16 may include a nickel-cobalt-chromium-molybdenum alloy (e.g., MP35-N). The proximal region 14 may be made from the same material as the distal region 16 or a different material such as stainless steel. These are just examples. Other materials are contemplated.

In some embodiments, the proximal region 14 and the distal region 16 are formed from the same monolith of material. In other words, the proximal region 14 and the distal region 16 are portions of the same tube defining the tubular member 12. In other embodiments, the proximal region 14 and the distal region 16 are separate tubular members that are joined together. For example, a section of the outer surface of the portions 14/16 may be removed and a sleeve 17 may be disposed over the removed sections to join the regions 14/16. Alternatively, the sleeve 17 may be simply disposed over the regions 14/16. Other bonds may also be used including welds, thermal bonds, adhesive bonds, or the like. If utilized, the sleeve 17 used to join the proximal region 14 with the distal region 16 may include a material that desirably bonds with both the proximal region 14 and the distal region 16. For example, the sleeve 17 may include a nickel-chromium-molybdenum alloy (e.g., INCONEL).

A plurality of slots 18 may be formed in the tubular member 12. In at least some embodiments, the slots 18 are formed in the distal region 16. In at least some embodiments, the proximal region 14 lacks slots 18. However, the proximal region 14 may include slots 18. The slots 18 may be desirable for a number of reasons. For example, the slots 18 may provide a desirable level of flexibility to the tubular member 12 (e.g., along the distal region 16) while also allowing suitable transmission of torque. The slots 18 may be arranged/distributed along the distal region 16 in a suitable manner. For example, the slots 18 may be arranged as opposing pairs of slots 18 that are distributed along the length of the distal region 16. In some embodiments, adjacent pairs of slots 18 may have a substantially constant spacing relative to one another. Alternatively, the spacing between adjacent pairs may vary. For example, more distal regions of the distal region 16 may have a decreased spacing (and/or increased slot density), which may provide increased flexibility. In other embodiments, more distal regions of the distal region 16 may have an increased spacing (and/or decreased slot density). These are just examples. Other arrangements are contemplated.

A sensor 20, which may take the form of a pressure sensor 20, may be disposed within the tubular member 12 (e.g., within a lumen of tubular member 12). While the pressure sensor 20 is shown schematically in FIG. 1, it can be appreciated that the structural form and/or type of the pressure sensor 20 may vary. For example, the pressure sensor 20 may include a semiconductor (e.g., silicon wafer) pressure sensor, piezoelectric pressure sensor, piezo resistive pressure sensor, capacitive pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor. In some of these and in other instances, the sensor 20 may take the form of or otherwise be capable of being a temperature sensor, a flow sensor, an acoustic sensor, an ultrasound sensor, or the like. These types of sensors, to the extent appropriate, may be utilized in any of the devices disclosed herein.

As indicated above, the pressure sensor 20 may include an optical pressure sensor. In at least some of these embodiments, an optical fiber or fiber optic cable 24 (e.g., a multimode fiber optic) may be attached to the pressure sensor 20 and may extend proximally therefrom. The optical fiber 24 may include a central core 60 and an outer cladding 62. In some instances, a sealing member (not shown) may attach the optical fiber 24 to the tubular member 12. Such an attachment member may be circumferentially disposed about and attached to the optical fiber 24 and may be secured to the inner surface of the tubular member 12 (e.g., the distal region 16). In addition, a centering member 26 may also be bonded to the optical fiber 24. In at least some embodiments, the centering member 26 is proximally spaced from the pressure sensor 20. Other arrangements are contemplated. The centering member 26 may help reduce forces that may be exposed to the pressure sensor 20 during navigation of guidewire and/or during use.

In at least some embodiments, the distal region 16 may include a region with a thinned wall and/or an increased inner diameter that defines a sensor housing region 52. In general, the sensor housing region 52 is the region of distal region 16 that ultimately "houses" the pressure sensor 20. By virtue of having a portion of the inner wall of the tubular member 12 being removed at the sensor housing region 52, additional space may be created or otherwise defined that can accommodate the sensor 20. The sensor housing region 52 may include one or more openings such as one or more distal porthole openings 66 that provide fluid access to the pressure sensor 20.

A tip member 30 may be coupled to the distal region 16. The tip member 30 may include a core member 32 and a spring or coil member 34. A distal tip 36 may be attached to the core member 32 and/or the spring 34. In at least some embodiments, the distal tip 36 may take the form of a solder ball tip. The tip member 30 may be joined to the distal region 16 of the tubular member 12 with a bonding member 46 such as a weld.

The tubular member 12 may include an outer coating 19. In some embodiments, the coating 19 may extend along substantially the full length of the tubular member 12. In other embodiments, one or more discrete sections of the tubular member 12 may include the coating 19. The coating 19 may be a hydrophobic coating, a hydrophilic coating, or the like. The tubular member 12 may also include an inner coating 64 (e.g., a hydrophobic coating, a hydrophilic coating, or the like) disposed along an inner surface thereof. For example, the hydrophilic coating 64 may be disposed along the inner surface of the housing region 52. In some of these and in other instances, the core member 32 may include a coating (e.g., a hydrophilic coating). For example, a proximal end region and/or a proximal end of the core member 32 may include the coating. In some of these and in other instances, the pressure sensor 20 may also include a coating (e.g., a hydrophilic coating).

Figure 2:
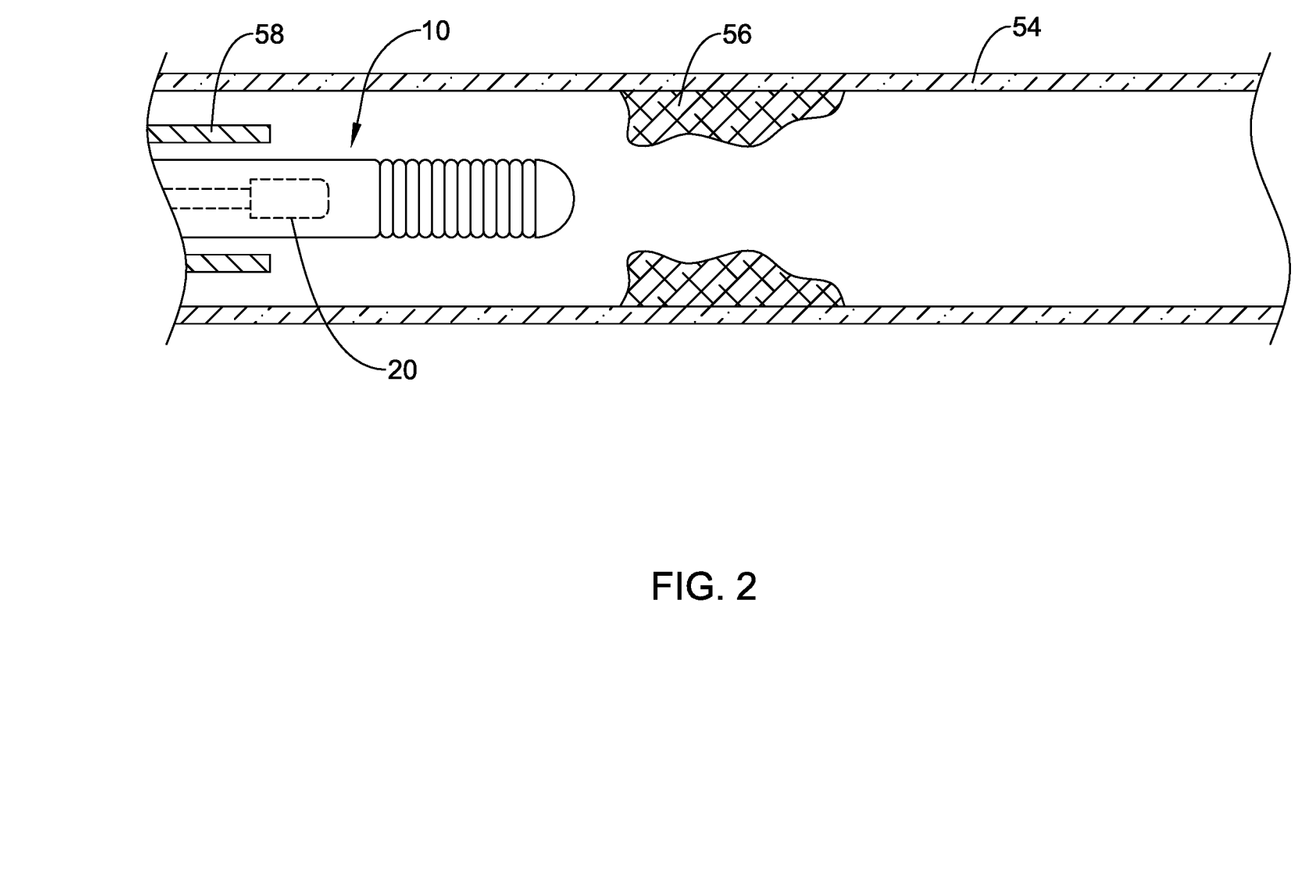
FIG. 2 is a partial cross-sectional view of an example medical device disposed at a first position adjacent to an intravascular occlusion.
Figure 3:
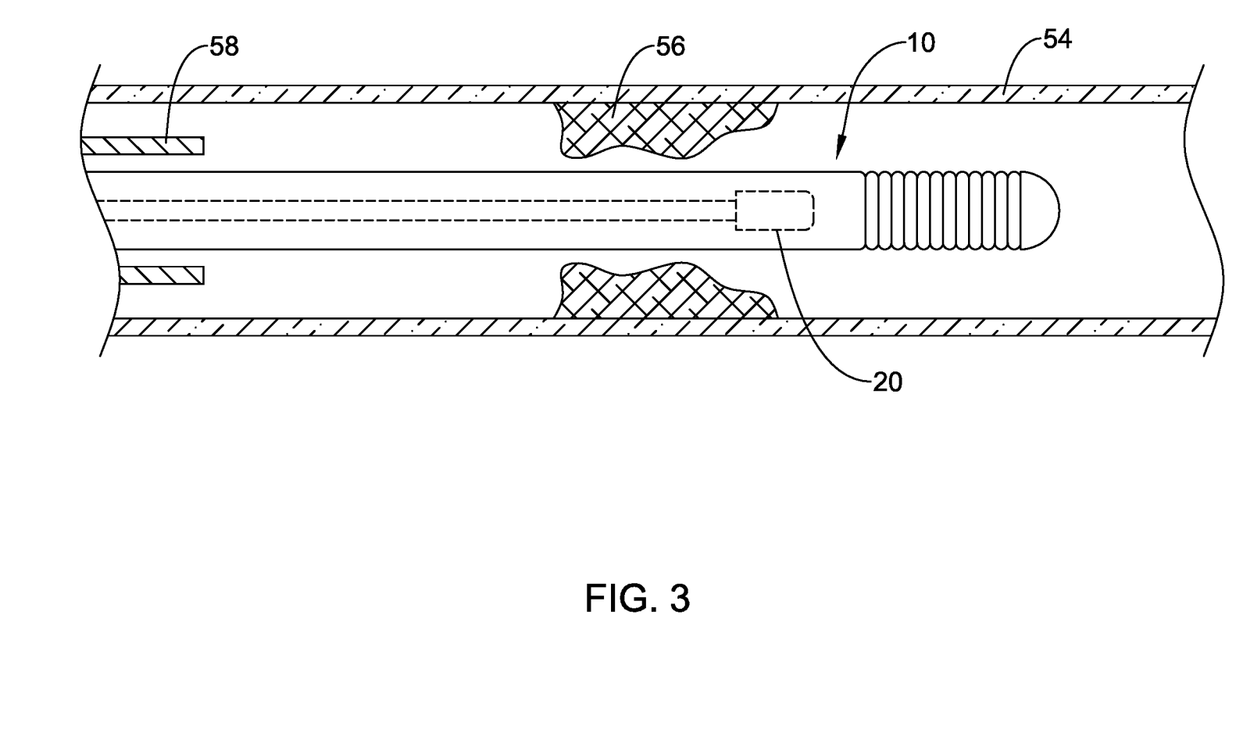
FIG. 3 is a partial cross-sectional view of an example medical device disposed at a second position adjacent to an intravascular occlusion.

In use, a clinician may use the guidewire 10 to measure and/or calculate FFR (e.g., the pressure after an intravascular occlusion relative to the pressure before the occlusion and/or the aortic pressure). Measuring and/or calculating FFR may include measuring the aortic pressure in a patient. This may include advancing guidewire the 10 through a blood vessel or body lumen 54 to a position that is proximal or upstream of an occlusion 56 as shown in FIG. 2. For example, the guidewire 10 may be advanced through a guide catheter 58 to a position where at least a portion of the sensor 20 is disposed distal of the distal end of the guide catheter 58 and measure the pressure within body lumen 54. This pressure may be characterized as an initial pressure. In some embodiments, the aortic pressure may also be measured by another device (e.g., a pressure sensing guidewire, catheter, or the like). The initial pressure may be equalized with the aortic pressure. For example, the initial pressure measured by the guidewire 10 may be set to be the same as the measured aortic pressure. The guidewire 10 may be further advanced to a position distal or downstream of the occlusion 56 as shown in FIG. 3 and the pressure within body lumen 54 may be measured. This pressure may be characterized as the downstream or distal pressure. The distal pressure and the aortic pressure may be used to calculate FFR.

Figure 4:
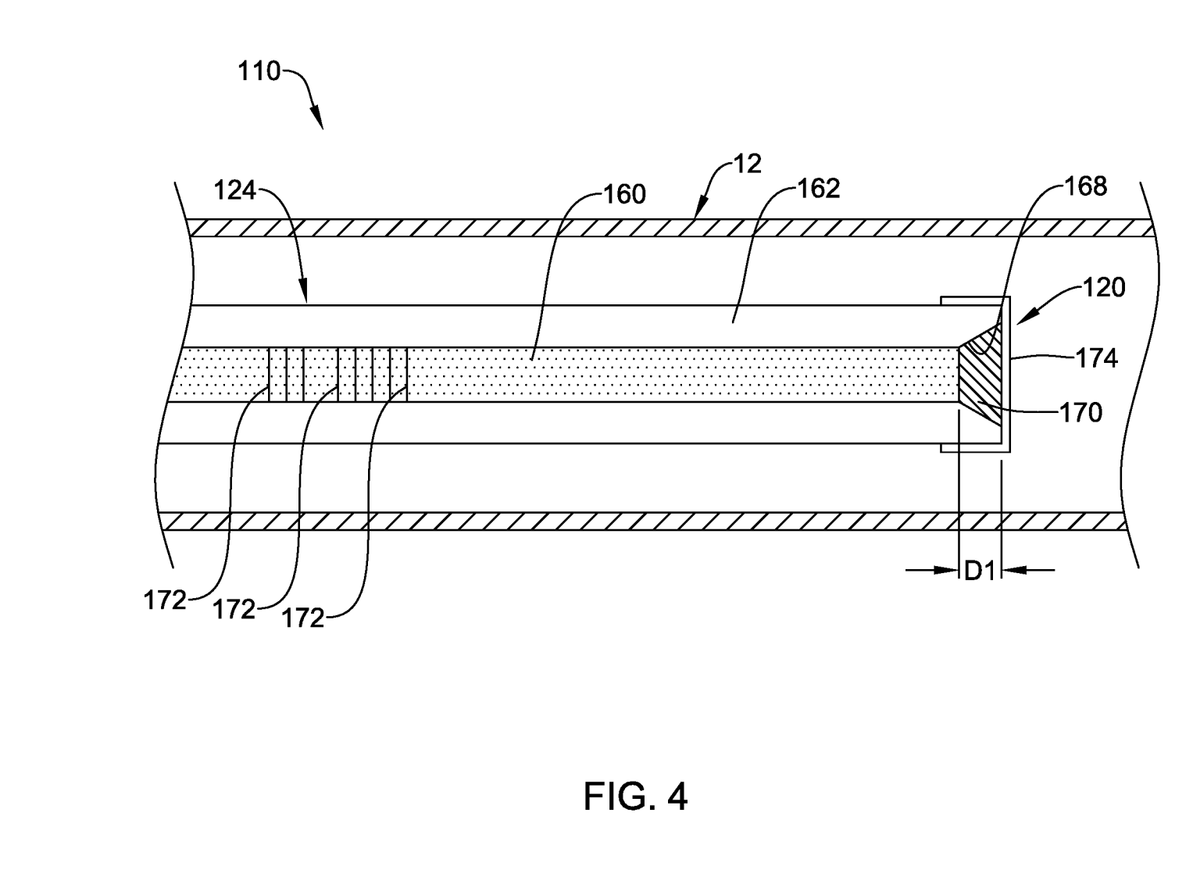
FIG. 4 illustrates a portion of an example medical device.

FIG. 4 illustrates another example medical device 110 that may be similar in form and function to other medical devices disclosed herein. The medical device 110 may include the tubular member 12 (e.g., including the structural features described and shown herein). An optical fiber 124 may be disposed within the tubular member 12. The optical fiber 124 may include a core 160 and a cladding 162. In some instances, a single mode optical fiber having an outer diameter of about 125 µm (e.g., and a 62.5 µm core 160) may be used. In other instances, a multimode optical fiber having an outer diameter of about 125 µm (e.g., and a 62.5 µm core 160) may be used. In other instances, a single mode optical fiber having an outer diameter of about 125 µm and a 62.5 µm core 160 may be spliced with another optical fiber having an outer diameter of 125 µm and a 105 µm core 160. In this example, the optical fiber with the larger core 160 may be used to form/define a sensor (e.g., a sensor 120 as discussed herein). In other instances, a multimode optical fiber having an outer diameter of about 125 µm and a 62.5 µm core 160 may be spliced with another optical fiber having an outer diameter of 125 µm and a 105 µm core 160. In this example, the optical fiber with the larger core 160 may be used to form/define a sensor (e.g., a sensor 120 as discussed herein). These are just examples. Optical fibers of various sizes are contemplated.

A pressure sensor 120 may be formed at a distal end region of the optical fiber 124. In this example, the pressure sensor 120 may be defined by forming a depression or cavity 168 in the optical fiber 124 and then disposing a polymeric member 170 within the cavity 176. In other words, the pressure sensor 120 may be formed without the need for a separate glass or micro optical mechanical system (MOMS) housing having a deflectable membrane. Instead, a low modulus, highly sensate, elastic material may be disposed within the cavity 168 to define the pressure sensor 120. The use of the pressures sensor 120 formed at the end of the optical fiber 124 may be desirable for a number of reasons. For example, the polymeric member 170 may be relatively sensitive to changes in pressure. This may provide a high level of sensitivity to the pressure sensor 170. In addition, by not having a separate sensor housing attached to the end of the optical fiber 124, the overall size of the medical device 110 may be reduced (e.g., the tubular member 12 may be smaller at least in part because it would not need to house the sensor housing). In at least some instances, the polymeric member 170 may extend to the bottom (e.g., the proximal end) of the cavity 168. The polymeric member 170 may then contact a portion of or all of the proximal end or edge of the cavity 168. The polymeric member 170 may extend distally and fill a portion of or all of the cavity 168. In some instances, a portion of the polymeric member 170 may extend distally beyond the distal end of the optical fiber 124. In other instances, the polymeric member 170 may terminate at the distal end of the optical fiber 124 (e.g., the polymeric member 170 and the optical fiber 124 are coterminous).

In some instances, the polymeric member 170 may include a dry film photosensitive material such as Ordyl SY300, ADEX/SY300, or SU-8, a liquid photosensitive material such as SU-8, polyimide (e.g., a film or a liquid photosensitive material), benzocyclobutene, a variety of non-photosensitive polymer films (e.g. such as polyethylene terephthalate, cyclic olefin copolymer, KAPTON, polydimethylsiloxane, poly(methyl methacrylate), or the like). Other materials are contemplated including those materials disclosed herein.

In some instances, the polymeric member 170 may be temperature sensitive. This may allow the sensor 120 to also or alternatively function as a temperature sensor. In some instances, one or more fiber Bragg gratings 172 may be disposed along the optical fiber 124. The fiber Bragg gratings may allow for temperature compensation.

A reflective member or coating 174 may be coupled to the polymeric member 170. In some instances, the coating 174 may include a metal, a polymer such as parylene, a vapor deposited material (e.g., an oxide, nitride, carbon material, or the like), etc. In some instances, the coating 174 may include a mirror or partial mirror that may be formed by sputtering a reflective material such as chromium, silver, zirconium dioxide, titanium dioxide or the like along the polymeric member 170. In some instances, the coating 174 may take the form of a singular layer of material. Alternatively, the coating 174 may include two or more separate, distinct layers of material (including the same or different materials).

Figure 5:
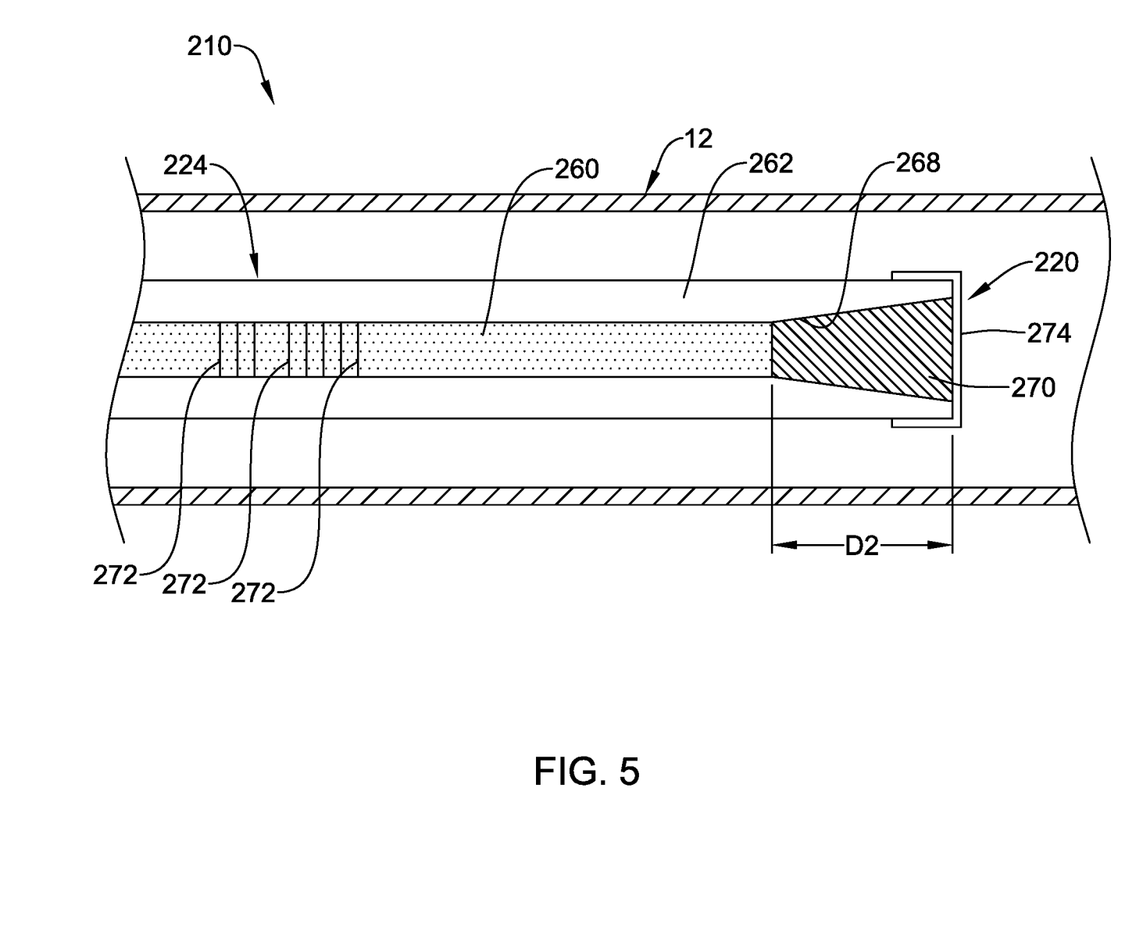
FIG. 5 illustrates a portion of an example medical device.

In some instances, the cavity 168 may have a depth D1. In some instances, the depth D1 may be on the order of about 1 μm to 100 μm. The depth, however, may vary. For example, FIG. 5 illustrates another example medical device 210 that may be similar in form and function to other medical devices disclosed herein, where the depth D2 of the cavity 268 is varied. In this example, the medical device 210 may include an optical fiber 224 having a cavity 268 formed therein. The cavity 268 may have a depth D2 on the order of about 100 μm to 500 μm. Varying the depth of the cavities 168/268 may allow for differences in sensitivity.

Much like the medical device 110, the medical device 210 may include the tubular member 12 (e.g., including the structural features described and shown herein). The optical fiber 224 may be disposed within the tubular member 12 and the optical fiber 224 may include a core 260 and a cladding 262. A pressure sensor 220 may be formed at a distal end region of the optical fiber 224. In this example, the pressure sensor 220 may be defined by the cavity 268 in the optical fiber 224 and a polymeric member 270 disposed within the cavity 276.

The medical device 210 may include other features similar to the medical device 110. For example, in some instances, one or more fiber Bragg gratings 272 may be disposed along the optical fiber 224. A reflective member or coating 274 may be coupled to the polymeric member 270.

In some instances, the coating 274 may include a metal, a polymer such as parylene, a vapor deposited material (e.g., an oxide, nitride, carbon material, or the like), etc. In some instances, the coating 274 may include a mirror or partial mirror that may be formed by sputtering a reflective material such as chromium, silver, or the like along the polymeric member 270. In some instances, the coating 274 may take the form of a singular layer of material. Alternatively, the coating 274 may include two or more separate, distinct layers of material (including the same or different materials).

A number of processes for fabricating pressure sensors are also contemplated. In one example fabrication process, the cavity 168/268 can be formed in the optical fiber 124/224. This may include etching an end region of the optical fiber using a suitable etching reagent such as HF (e.g., HF in isopropyl alcohol). In some instances, the etching reagent may preferentially etch the core (e.g., the core 160/260) of the optical fiber 124/224 rather than or more rapidly than the cladding (e.g., the cladding 162/262).

The process may also include disposing the polymeric member 170/270 into the cavity 168/268. In some instances, this may include an inkjet process where the polymeric material 17/270 is directly into the cavity.

Another example process for disposing the polymeric member 170/270 into the cavity 168/268 may include spinning on a sacrificial layer of material (e.g., a photoresist) onto a dummy wafer (e.g., a dummy silicon wafer), baking the dummy wafer with the sacrificial layer, and spinning on a layer of polymeric material onto the sacrificial layer. The etched optical fibers 124/224 may be pushed onto the layer of polymeric material and the material may be cured (e.g., thermally cured, cured with ultraviolet light, or the like).

Another example process for disposing the polymeric member 170/270 into the cavity 168/268 may include aligning and inserting the etched optical fibers 124/224 onto a dummy wafer (e.g., a dummy silicon wafer) having a plurality of pillars (e.g., etched pillars) formed therein, applying a hydrophobic or anti-stiction coating to areas where it is desired to not have the polymer material, apply the polymer material (e.g., dip, spray, print, or the like), wash off any excess polymer, and bake and/or cure the material.

Another example process may include depositing, masking, and curing a photosensitive liquid polymer layer (e.g., such as SU-8) onto the end of the optical fiber 124/224 and then adding an external reflective member or coating (e.g., the coating 174/274). Alternatively, non-glass cavity walls could be formed using a photo-sensitive dry-film layer.

The materials that can be used for the various components of the guidewire 10 (and/or other guidewires disclosed herein) and the various tubular members disclosed herein may include those commonly associated with medical devices. For simplicity purposes, the following discussion makes reference to the tubular member 12 and other components of the guidewire 10. However, this is not intended to limit the devices and methods described herein, as the discussion may be applied to other tubular members and/or components of tubular members or devices disclosed herein.

The tubular member 12 and/or other components of the guidewire 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the guidewire 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the guidewire 10 to achieve the same result.

In some embodiments, a degree of Magnetic Resonance Imaging (MRI) compatibility is imparted into the guidewire 10. For example, the guidewire 10, or portions thereof, may be made of a material that does not substantially distort the image and create substantial artifacts (e.g., gaps in the image). Certain ferromagnetic materials, for example, may not be suitable because they may create artifacts in an MRI image. Guidewire 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A pressure sensing medical device, comprising:
   a tubular member having a proximal region and a housing region;
   an optical fiber disposed within the tubular member and extending to the housing region, the optical fiber having a distal end region with a cavity formed therein;
   a polymeric member disposed within the cavity;
   wherein the polymeric member substantially fills the cavity; and
   a reflective surface disposed along the polymeric member.

2. The pressure sensing medical device of claim 1, wherein the proximal region of the tubular member has a first inner diameter, wherein the housing region of the tubular member has a second inner diameter, and wherein the first inner diameter is different from the second inner diameter.

3. The pressure sensing medical device of claim 2, wherein the first inner diameter is smaller than the second inner diameter.

4. The pressure sensing medical device of claim 3, wherein the tubular member has a substantially constant outer diameter.

5. The pressure sensing medical device of claim 1, wherein the optical fiber has a substantially constant outer diameter.

6. The pressure sensing medical device of claim 1, wherein one or more fiber Bragg gratings are disposed along the optical fiber.

7. The pressure sensing medical device of claim 1, wherein the reflective surface includes a coating disposed along the polymeric member.

8. The pressure sensing medical device of claim 7, wherein the coating includes a metal.

9. The pressure sensing medical device of claim 7, wherein the coating is disposed at a distal end of the polymeric member.

10. A pressure sensing guidewire, comprising:
    a tubular member having a proximal region and a pressure sensor housing region;
    an optical fiber disposed within the tubular member and extending to the pressure sensor housing region;

wherein a pressure sensor is defined by a polymer-filled cavity at a distal end region of the optical fiber; and a reflective coating disposed along at least a portion of the pressure sensor.

11. The pressure sensing guidewire of claim 10, wherein the proximal region of the tubular member has a first inner diameter, wherein the pressure sensor housing region of the tubular member has a second inner diameter, and wherein the first inner diameter is different from the second inner diameter.

12. The pressure sensing guidewire of claim 11, wherein the first inner diameter is smaller than the second inner diameter.

13. The pressure sensing guidewire of claim 12, wherein the tubular member has a substantially constant outer diameter.

14. The pressure sensing guidewire of claim 10, wherein the optical fiber has a substantially constant outer diameter.

15. The pressure sensing guidewire of claim 10, wherein one or more fiber Bragg gratings are disposed along the optical fiber.

16. The pressure sensing guidewire of claim 10, wherein the reflective coating includes a metal.

17. The pressure sensing guidewire of claim 10, wherein the reflective coating is disposed at a distal end of the pressure sensor.

18. A method for manufacturing a pressure sensing guidewire, the method comprising:

forming a cavity along a distal end region of an optical fiber;

disposing a polymeric member within the cavity;

coupling a reflective member to the polymeric member to form a pressure sensor;

wherein the polymeric member substantially fills the cavity; and disposing the pressure sensor within a housing region of a tubular member.

19. The method of claim 18, further comprising disposing one or more fiber Bragg gratings along the optical fiber.

* * * * *